(12) United States Patent
Kiehne

(10) Patent No.: US 7,854,722 B2
(45) Date of Patent: Dec. 21, 2010

(54) SYRINGE WITH REMOVABLE NEEDLE

(75) Inventor: Bruce Leigh Kiehne, Springwood (AU)

(73) Assignee: Occupational & Medical Innovations Ltd., Queensland (AU)

( * ) Notice: Subject to any disclaimer, the term of this patent is extended or adjusted under 35 U.S.C. 154(b) by 0 days.

(21) Appl. No.: 11/919,121

(22) PCT Filed: May 5, 2006

(86) PCT No.: PCT/AU2006/000598

§ 371 (c)(1), (2), (4) Date: Oct. 24, 2007

(87) PCT Pub. No.: WO2006/119551

PCT Pub. Date: Nov. 16, 2006

(65) Prior Publication Data

US 2009/0093760 A1 Apr. 9, 2009

(30) Foreign Application Priority Data

May 11, 2005 (AU) ............................... 2005902357

(51) Int. Cl.
*A61M 5/00* (2006.01)
(52) U.S. Cl. ..................................... 604/110
(58) Field of Classification Search .................. 604/110
See application file for complete search history.

(56) References Cited

U.S. PATENT DOCUMENTS

| | | |
|---|---|---|
| 4,650,468 A | 3/1987 | Jennings, Jr. |
| 4,932,939 A | 6/1990 | Magre et al. |
| 5,222,944 A | 6/1993 | Harris |
| 5,431,632 A | 7/1995 | Lu |
| 5,899,887 A | 5/1999 | Liu |
| 5,976,108 A | 11/1999 | Liu |
| 6,228,054 B1 | 5/2001 | Dysarz |
| 6,547,762 B1 | 4/2003 | Botich et al. |
| 2002/0193736 A1* | 12/2002 | Kiehne ....................... 604/110 |
| 2005/0124933 A1 | 6/2005 | Segal |

FOREIGN PATENT DOCUMENTS

| | | |
|---|---|---|
| CA | 2452673 | 6/2004 |
| EP | 0 634 183 | 1/1995 |
| WO | WO 90/11099 | 10/1990 |
| WO | WO 2004/105842 | 12/2004 |

* cited by examiner

*Primary Examiner*—Nicholas D Lucchesi
*Assistant Examiner*—Victoria P Campbell
(74) *Attorney, Agent, or Firm*—Hoffman, Wasson & Gitler, P.C.

(57) ABSTRACT

A medical syringe has a needle shoot back mechanism which can be triggered to shoot the used needle back into the safety of the syringe body and is of a special design to allow the needle to be replaced without affecting the efficiency of the shoot back mechanism. A rotatable cover member is also available which is relatively large and which can be more easily gripped and turned to remove the needle from the syringe.

9 Claims, 6 Drawing Sheets

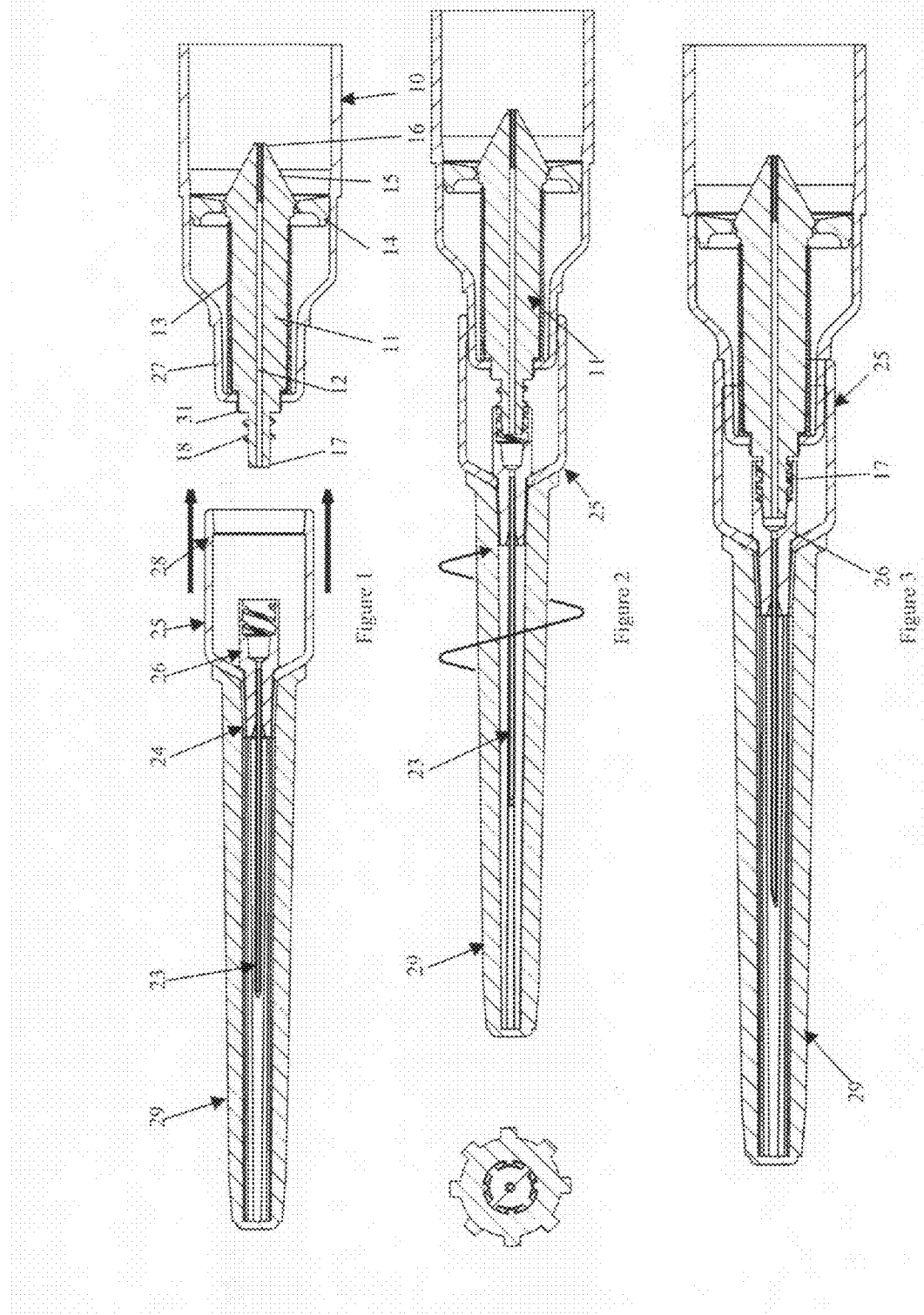

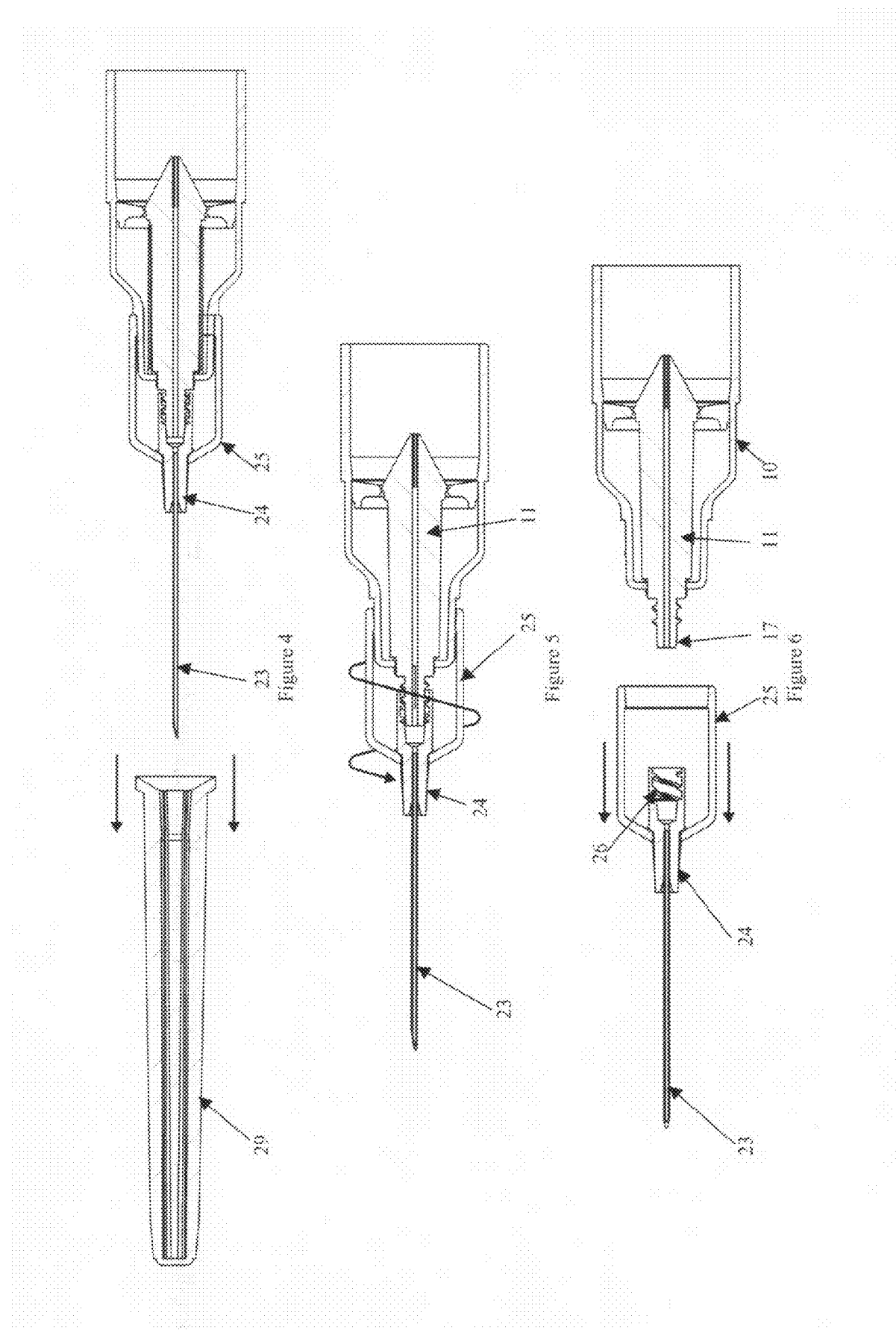

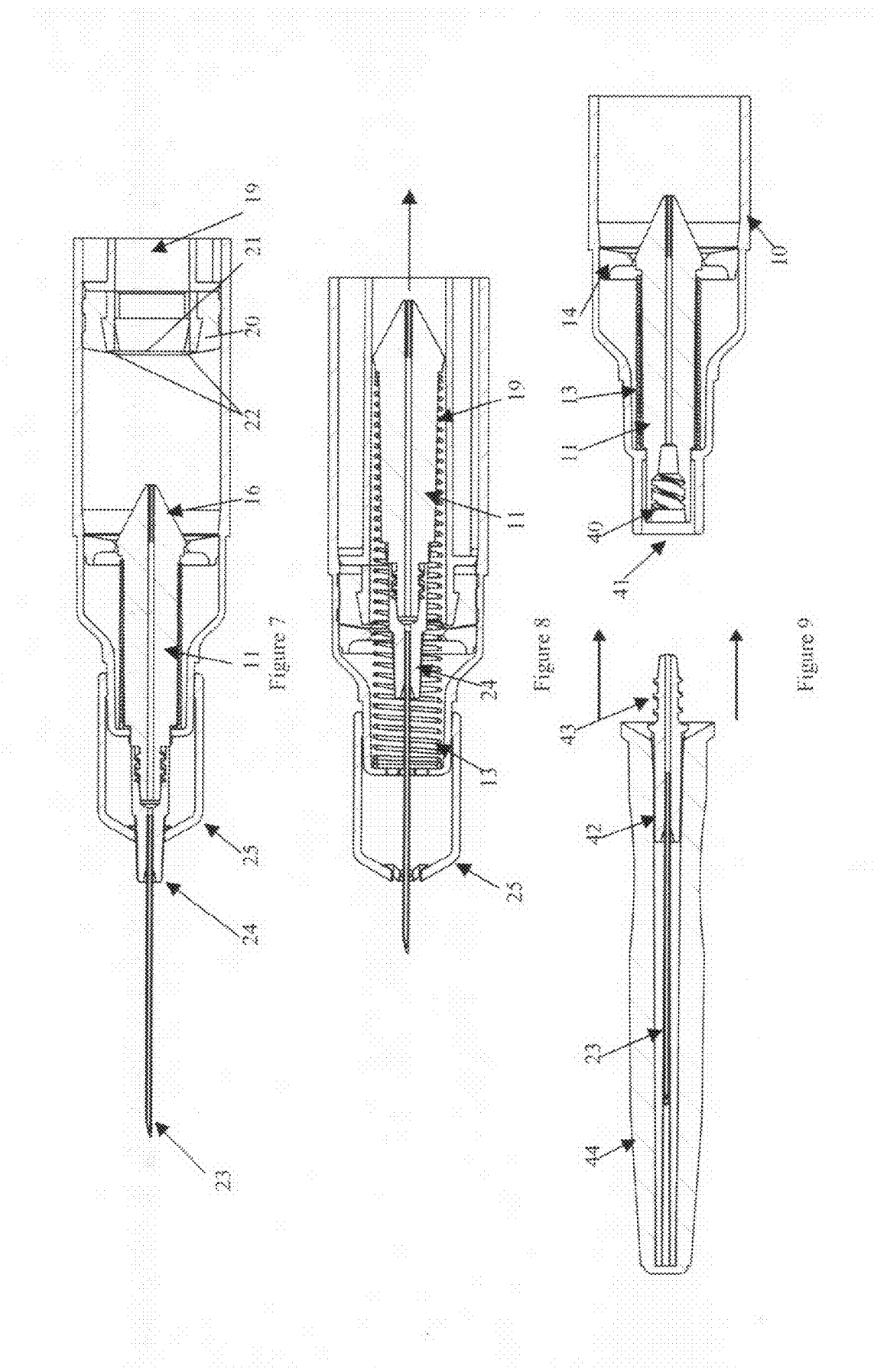

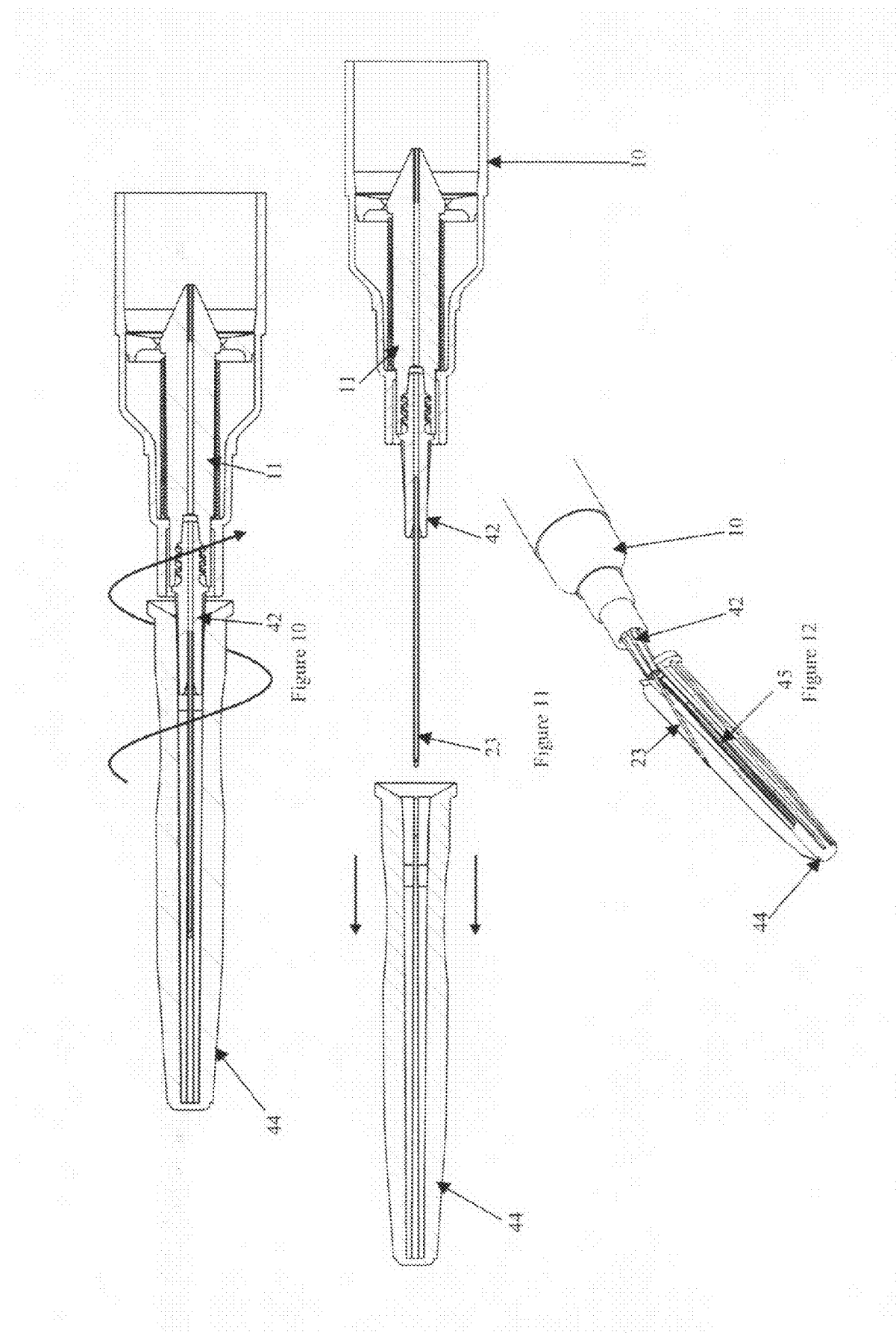

SYRINGE WITH REMOVABLE NEEDLE

FIELD OF THE INVENTION

This invention is directed to a medical device (for instance a syringe) of the type that has a needle. The invention is particularly directed to a needle containing medical device of the type that has a retractable or "shoot back" needle, and which enables the needle to be removed and replaced with a different needle without interfering with the efficiency of the needle retraction mechanism.

BACKGROUND ART

It is well-known that a common source of injury to medical workers is needlestick injury. Needlestick injury occurs when a contaminated needle accidentally cuts a medical worker. Therefore, it is known to provide a needle containing medical device (typically a syringe) with a needle that is retracted into the syringe body after use to reduce or eliminate needlestick injury.

Another advantage in providing a retractable needle is to prevent the needle from being reused.

There are many types of mechanisms to enable a medical needle to be retracted into the syringe body.

One type of mechanism has the needle biased by a small helical spring. The needle is prevented from shooting back into the syringe body by some form of needle holding mechanism. The plunger contains some form of cutting mechanism, and when the plunger is pushed hard against the front of their syringe, the cutting mechanism cuts the needle holding mechanism to enable the needle to be shot back into the syringe body. This type of arrangement can be called a "cutting" arrangement.

Another type of mechanism does not require a spring around the syringe. Instead, the plunger is under vacuum. When the plunger is pushed hard against a front of the syringe, the plunger seal decouples from the front of the plunger and the plunger seal also attaches to the needle. Once the plunger seal is released from the front of the plunger, the vacuum in the plunger will suck back the plunger seal+the attached needle.

Another type of arrangement uses a spring that is behind the plunger seal such that as the plunger is pushed forwardly, the spring is tensioned. Again, as the plunger is pushed hard against the front of the syringe, the front of the plunger couples with the needle and the spring then pulls the plunger+ the needle back into the syringe body.

A reliable mechanism is described in our earlier international patent application PCT/AU01/00183. This mechanism contains a needle which is biased by a small helical spring. The needle is attached to a needle holder. The needle holder is held in place against the bias of the spring by a small holding member that contains an outer part and an inner part that are separated by a frangible portion. When the plunger is pushed against the front of the syringe, the plunger will push the outer part forwardly while the inner part cannot move and this causes the frangible portion to break. Once this happens, the needle shoots back into the plunger body and pierces through the relatively thin plunger seal by the bias of the spring. This type of mechanism can be seen as a "stretch and break" mechanism as opposed to a cutting mechanism and is more reliable in use.

With needle containing medical devices such as syringes, irrespective of whether the syringe contains a retraction mechanism, there is often the need to replace the needles. As an example, when injecting the fluid, a larger diameter needle can be attached to the syringe to draw the fluid into the syringe body more quickly. Because the larger diameter needle can cause more pain to a patient, once the fluid is in the syringe body, the larger diameter needle can be removed and a smaller injecting needle is attached.

Attachment and removal of needles can cause needlestick injury, and even if the needle is not contaminated, a needlestick injury can still be quite painful. Therefore, there would be an advantage if it were possible to replace needles while reducing needlestick injury.

As syringes with shoot back needles are becoming more popular, these syringes will also require the needles to be replaced. However, syringes with shoot back mechanisms have the needle fixed to some part of the shoot back mechanism and replacement of the needle is not possible. Also, there is a danger that if the needle is made replaceable, this will make the shoot back mechanism less reliable or even in operable. Therefore, there would be an advantage if it were possible to have a needle containing medical device of the type where the needle can be retracted after use and where the needle can also be replaced prior to retraction and without unnecessarily interfering with the efficiency of the retraction mechanism.

Many syringes that do not have a retraction mechanism allow the needle to be replaced. This is a very conventional but suffers from the disadvantage that the parts can be quite small and removing the needle from the front of the syringe can be quite difficult especially if wearing gloves, if the surfaces are wet or contaminated and the like. Therefore, there would be an advantage if it were possible to provide a design that would enable needles to be removed and replaced in a more convenient manner.

It will be clearly understood that, if a prior art publication is referred to herein, this reference does not constitute an admission that the publication forms part of the common general knowledge in the art in Australia or in any other country.

OBJECT OF THE INVENTION

It is an object of the invention to provide a needle containing medical device of the type that enables the needle to be replaced, and particularly when the medical device contains some form of needle retraction mechanism such as a shoot back mechanism.

In a broad form, the invention resides in a needle containing medical device, the medical device comprising:
  A needle assembly which contains a needle and a needle holder to which the needle is attached,
  A housing,
  A body at least partially in the housing and which has attachment means to releasably attach to the needle holder thereby enabling the needle assembly to be removed from the body and another needle assembly to be attached to the body, and
  a cover member that extends about the needle holder such that the needle holder is at least partially within the cover member, the cover member adapted for releasable attachment to the housing.

In another form, the invention resides in a needle containing medical device, the medical device comprising a body to which the needle is attached, the body containing needle attachment means, and a needle assembly, the assembly comprising a needle, a needle holder to which the needle is attached, the holder containing attachment means to attach the holder to the body, and a cover member that extends about the needle holder such that the attachment means on the holder is within the cover member, the cover member adapted for releasable attachment to a front of the body.

In this manner, the needle assembly can be held using the cover member which provides a much larger surface to enable the needle to be attached and removed from the front of the medical device in a simpler and easier manner.

Manipulation of the larger and easier to handle cover member [typically by rotation] can remove the needle assembly from the housing [typically the front of the syringe barrel] and another needle assembly can then be reattached. This mechanism is considered to be better than trying to grip and release the quite small needle holder directly.

Typically, the medical device will comprise a syringe, and the invention will be described with reference to the medical device as a syringe, although it should be appreciated that no particular limitation is meant thereby and the invention may be applicable to medical devices of the type containing a medical needle.

It is preferred that the needle holder is threadingly attached to the front of the housing [typically the barrel of a medical device such as a syringe]. Thus, the front of the syringe may contain a threaded male portion and the needle holder may contain a threaded female (socket) portion, to enable the needle holder to be twisted on to the front of the syringe.

It is preferred that the attachment and removal is done via a mechanism that enables the needle holder to move slightly towards and away from the front of the syringe during the attachment/removal action. A threaded arrangement provides this motion. However, it is considered that any other type of attachment that provides this motion may also form part of the invention.

The assembly may further comprise a cap. The cap will typically extend about the needle and will typically be removeably attached such that the cap can be removed to expose the needle. The cap may be removeably attached by any suitable mechanism including some form of press fit arrangement, a twist lock arrangement, some form of friction fit arrangement and the like. It is not considered that any particular limitation should be placed on the invention merely by the means by which the cap is attached to the remainder of the assembly.

If the medical device comprises a syringe, the syringe will typically comprise a syringe barrel and a plunger that slides within the syringe barrel. The barrel will typically comprise a forward portion which is narrowed and contains a front most opening.

The syringe can be of any suitable length and diameter depending on the use and will typically comprise a syringe that can hold a volume of between 1-100 ml of fluid. This of course can vary to suit. The syringe can be made of any suitable material and will typically be made of plastics as is common in the manufacture of syringes.

The plunger will typically contain a front seal to prevent fluid from leaking past the plunger, this being common for syringes. The plunger will preferably contain a passageway, and it is convenient that this is done by simply making the plunger substantially hollow and cylindrical. However, a passageway can also be achieved by making the plunger with an X type cross-section and the like. The passageway is useful should the syringe contain some form of shoot back mechanism as will be described in greater detail below. The plunger will typically be made of plastics as is common in the manufacture of plungers.

If the medical device/syringe contains a needle retraction mechanism, it is preferred that the mechanism is of the type described in our earlier international patent application. This mechanism has a shoot back assembly that comprises a body which is typically substantially cylindrical and contains a passageway therethrough to enable fluid to pass through the needle, through the passageway and into the syringe barrel. The body is biased by a spring which will typically be a helical spring wound about the body. The body is held in the front of the syringe by a release mechanism. The release mechanism typically comprises an outer part that is held by the syringe barrel, and an inner part that is attached to the body, and a frangible portion that extends between the outer part and the inner part. The arrangement is such that when the plunger is pushed forwardly, the front of the plunger pushes against the outer part and pushes the outer part forwardly. The inner part cannot move and therefore movement of the outer part relative to the inner part breaks the frangible portion. As soon as a frangible portion is broken, the spring is released and the body is shot back into the plunger.

While it is preferred that the syringe contains a needle retraction mechanism of the type described above, it is considered that other types of retraction mechanisms may also be used.

Suitably, the syringe contains a shoot back mechanism of the type described above, and the body has a projection that extends through the front opening in the barrel and to which the needle assembly can be coupled. The projection may contain some form of attachment means, and it is preferred that the attachment means comprises some form of threading arrangement. The threads may be continuous or discontinuous and pitch of the thread may vary.

The needle assembly contains a needle holder. The needle holder contains attachment means to enable the needle holder to be attached to the syringe, and typically to the projection of the body that extends through the front opening of the barrel.

It is preferred that the attachment means comprises a female threaded socket which can attach to the threaded projection on the body.

The cover member on the needle assembly will typically be open ended such that the cover member can pass over the front portion of the syringe barrel. The size and shape of the cover member can vary but it is preferred that the size and shape is such that the cover member can be comfortably gripped by a medical practitioner to enable the needle is to be safely attached and removed. Thus, the cover member may be slightly smaller than the diameter of the syringe barrel.

The cover member will typically extend about and over the female socket on the needle holder.

It is preferred that the cover member is attached to the needle holder in a particular manner. The manner is preferably such that rotation of the cover member will cause rotation of the needle holder and therefore attachment/removal of the needle holder to the front of the syringe. However, the cover member is also preferably attached in such a manner that the needle holder can slide forwardly and rearwardly at least by a few millimetres relative to the cover. The reason for this will be described in greater detail below. Thus, the outside of the needle holder may be provided with grooves, and the cover member may be provided with projections that pass into the grooves such that rotation of the cover member causes rotation of the needle holder but the needle holder can slide longitudinally relative to the cover member. Of course, other attachment mechanisms are envisaged that enable the needle holder to slide relative to the cover member while still rotating with the cover member.

An advantage of the particular preferred means by which the cover member is attached to the needle holder is to (a) not to interfere with the needle shoot back mechanism and (b) enable a needle to be removed using the cover member as a gripping portion.

Another advantage may be that the needle can be removed by rotating the cover member. This is different to the common mechanism where the needle is simply press fitted to the front of the syringe and needs to be pulled off, this action risking a needle stick injury. With the cover member, it is considered safer to grip and turn the cover member to release the needle from the front of the syringe as opposed to the conventional mechanism where it is necessary to grip and pull the needle away from the front of the syringe.

To facilitate these advantages, it is preferred that a small locking means or releasable locking means or other type of releasable attachment means is provided between the cover member and the needle holder to temporarily lock the needle holder against sliding movement relative to the cover member. This temporary locking is advantageous in the removal action.

Thus, it is preferred that the cover member and the locking means are arranged such that as a needle is removed from the front of the syringe, the locking means is engaged to lock the cover member to the needle holder against relative sliding movement, but when the needle is attached to the front of the syringe, the locking means is not engaged to not hinder the shoot back mechanism. This will be described in greater detail below.

If the medical device/syringe contains a needle retraction mechanism, most mechanisms, and also the one described in our earlier patent application must not be rotated as any twisting or rotated movement can cause the frangible portion to snap causing premature release of the shoot back mechanism. However, it is preferred that the needle is attached to the retraction mechanism using a twist thread and therefore a rotative force can be applied, which is undesirable. Therefore, for this type of assembly, it is preferred that the retraction mechanism is held against rotation relative to the syringe barrel. The various types of ways are envisaged by which this can be achieved. In a simple arrangement, the portion of the retraction mechanism that projects from the front of the syringe barrel may contain projections/ribs/splines that engage into corresponding grooves immediately about the opening to prevent rotation but still allow sliding movement (e.g. retraction). Of course, in an alternative, the retraction mechanism may contain the recesses and the opening may contain the projections etc. Combinations are also envisaged. It is also envisaged that some form of anti-rotation mechanism may comprise a projection that abuts against a shoulder portion to prevent rotation but to allow retraction. It is not considered that any particular limitation should be placed on the invention merely by the means by which rotation is prevented while retraction is allowed.

In another form, the invention resides in a needle containing medical device, the medical device comprising a body to which the needle is attached, the body containing needle attachment means, and a needle assembly, the assembly comprising a needle, a needle holder to which the needle is attached, the holder containing attachment means to attach the holder to the body.

In this form of the invention, a cover member need not be required. In this form of the invention, the body may also comprise a syringe and the syringe may contain a needle retraction mechanism having a body that contains a socket which contains the needle attachment means, and the needle assembly may contain a needle holder formed with a projection which engages into the socket on the body.

BRIEF DESCRIPTION OF THE DRAWINGS

Embodiments of the invention will be described with reference to the following drawings in which:

FIG. 1. Illustrates a first embodiment of the invention which comprises a forward portion of a syringe barrel containing a shoot back mechanism, and a needle assembly which is about to be coupled to the front of the syringe barrel.

FIG. 1A. Particularly illustrates the anti-rotations from the arrangement of FIG. 1.

FIG. 2. Illustrates the arrangement of FIG. 1, but where the needle assembly is in the process of being threadingly attached to the front of the syringe.

FIG. 3. Illustrates the needle assembly fully attached to the front of the syringe but with the needle cap still on the needle.

FIG. 4. Illustrates the cap removed from the needle to expose the puncture needle.

FIG. 5. Illustrates the initial steps of removing the needle from the front of the syringe by rotating the cover member.

FIG. 6. Illustrates the needle being removed from the front of the syringe.

FIG. 7. Illustrates the needle attached to the front of the syringe and particularly illustrates the plunger moving forwardly towards a front of the syringe.

FIG. 8. Illustrates the shoot back mechanism in progress with the needle holder being attached to the body of the shoot back mechanism and a body in the process of shooting back into the plunger body to retract the needle.

FIG. 9. Illustrates a second embodiment of the invention and illustrates a needle assembly about to be attached to the front of a barrel.

FIG. 10. Illustrates the needle assembly attached to the front of the barrel.

FIG. 11. Illustrates the needle cap being pulled off.

FIG. 12. Particularly illustrates the design of the needle cap.

BEST MODE

Figure 13:
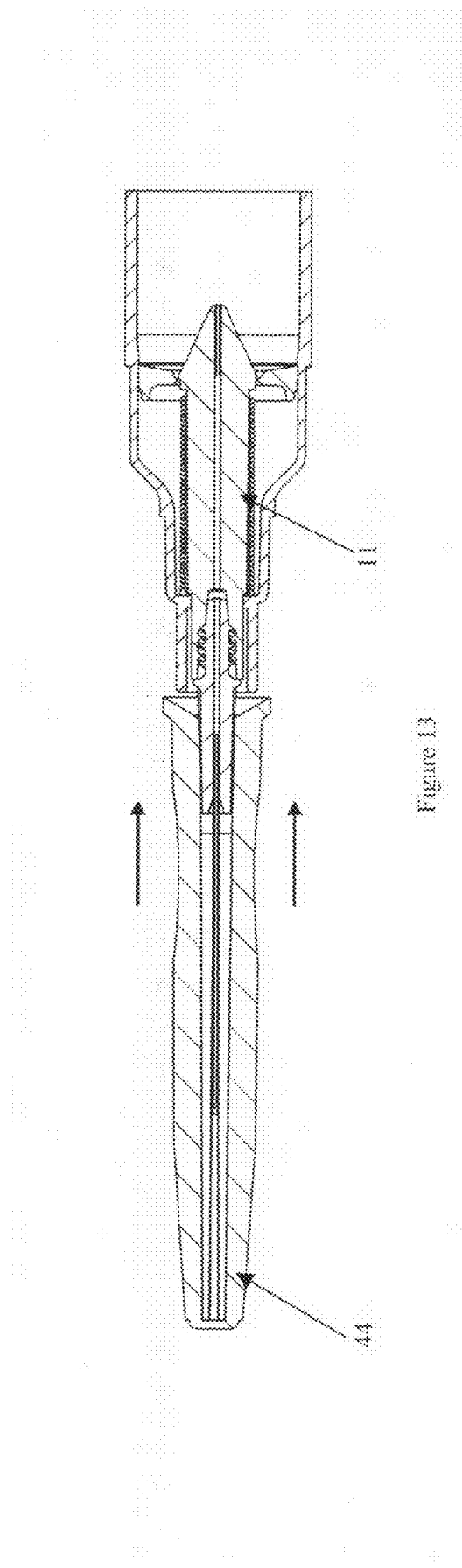
FIG. 13. Illustrates reattachment of the cap prior to removal of the needle.
Figure 14:
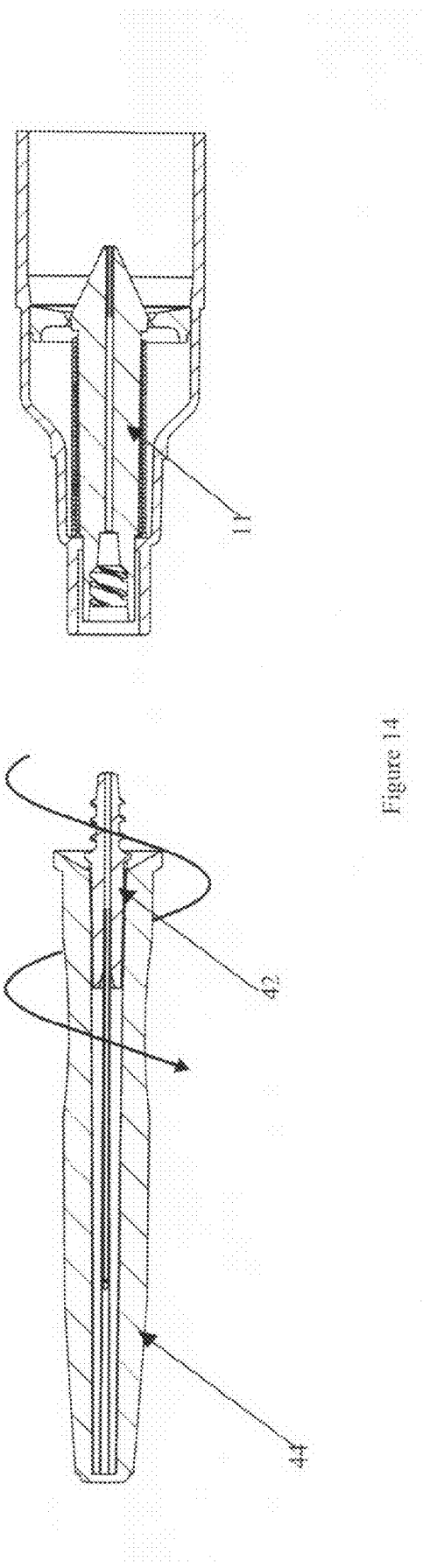
FIG. 14. Illustrates removal of the needle.
Figure 15:
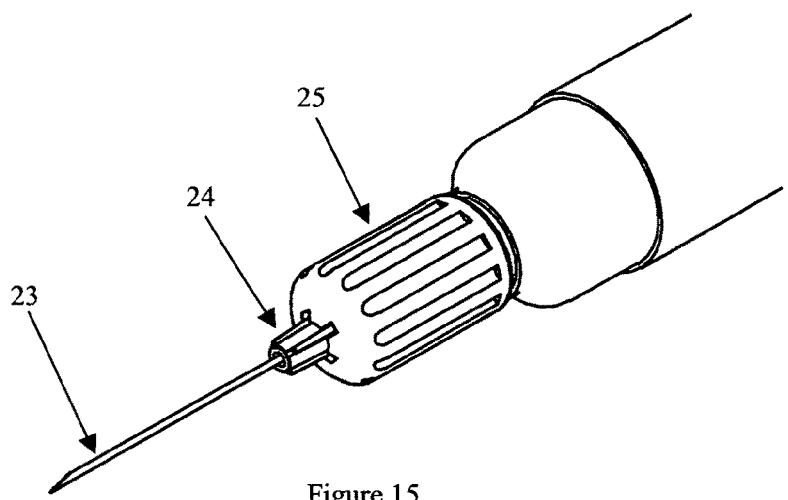
FIG. 15. Illustrates a front portion of the syringe.

Referring to the drawings, and initially to the first embodiment of the invention illustrated in FIGS. 1-8, and particularly initially to FIG. 1, there is illustrated the main parts of the invention. In the particular embodiment, the medical device comprises a syringe. The main parts illustrated in FIG. 1 comprises a front portion of the syringe barrel 10, a shoot back mechanism in the front portion of the syringe barrel and which comprises a body 11 containing a longitudinal passageway 12 to enable fluid to pass through the body, a biasing means in the form of a helical spring 13 which extends about the body and which is under compression. The body is held in place by a retaining ring 14 that extends about the body. The retaining ring is attached to the body by a frangible portion 15. Body 11 contains an inner end which has an "arrowhead" type configuration 16 and which extends into barrel 10, and an outer end which comprises a projection 17 which extends through a front opening in barrel 10. Projection 17 contains threads 18.

Although the main feature of the present invention is the ability of the needle to be attached and removed from the front of the syringe, at this stage, the retraction mechanism will be explained. Referring initially to FIG. 7, there is illustrated the plunger 19 moving forwardly through barrel 10 and towards the body 11 of the shoot back mechanism. Plunger 19 is hollow and contains the usual outer seal 20 but also contains a thin covering seal 21 extending over the front of the hollow plunger. As the plunger moves further forwardly, the inner end 16 (arrowhead shape) will push against seal 21 and will cause the seal to deform inwardly and will also cause the seal to stretch and weaken. This is necessary as ultimately the shoot back mechanism (body 11) will puncture through seal 21 and shoot back into the interior of hollow plunger 19. As plunger 19 moves further forwardly, the hard annular edge 22 of the plunger will abut against ring 14 and further pushing of plunger 19 will cause edge 22 to push ring 14 forwardly. This will cause the frangible portion 15 to break. As soon as this happens, body 11 is now released and spring 13 will cause body 11 to shoot through or past the seal 21 and into the inside of plunger 19. This is illustrated in FIG. 8.

Referring now to FIG. 1, the needle forms part of a needle assembly. The needle assembly comprises the puncture needle 23. The inner end of the puncture needle is attached to a needle holder 24. The needle holder itself has an inner end that comprises a socket 26 that has internal threads which are adapted to engage with threads 18 on projection 17 on the front of body 11.

Attached to needle holder 24 is a cover member 25. Cover member 25 is open ended such that it can pass over the front narrower portion of barrel 10, this being illustrated at least in FIGS. 2-3. The outside of the narrower portion of barrel 10 contains a small rib 27 which is adapted to engage with a small shoulder 28 on the cover member 25 when the cover member 25 is pushed on to the front of the barrel 10. Thus, the cover member 25 can be releasably held to the front of the barrel 10.

The cover member 25 is attached to the needle holder 24 in such a manner that rotation of the cover member 25 causes rotation of the needle holder 24 and thereby threading attachment of the needle holder 24 to projection 17. However, the attachment is also such that the needle holder 24 can be retracted into the syringe without hindrance by the cover member 25. Thus, it is envisaged that the cover member 25 will contain a rib/spline or button etc. that sits within a groove on the outside of the needle holder 24 such that rotation of the cover member 25 will cause rotation of the needle holder 24 but retraction of the needle holder 24 relative to the cover member 25 is allowed.

Finally, a cap 29 is provided to protect needle 23 during the initial attachment.

Referring to FIGS. 2-3, it can be seen that a person can grip the more comfortable and larger cover member 25 and push the cover member 25 onto the front of barrel 10. This causes projection 17 to pass into socket 26. The cover member 25 can then be rotated to cause the needle holder 24 to be threaded onto the projection 17. This arrangement is illustrated in FIG. 3.

Once attached, cap 29 can be pulled off needle holder 24, this being illustrated in FIG. 4. Cap 29 is lightly attached or can clip on to needle holder 24 by any suitable type of clipping mechanism which will typically comprise a small projection either on the cap or needle holder that press fits into a small recess. This stops the cap from inadvertently sliding off the needle assembly.

Figure 16:
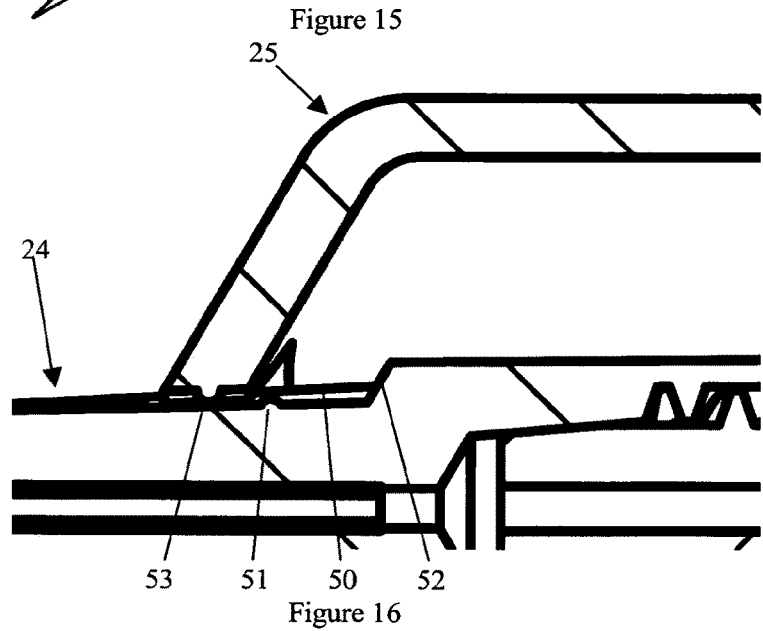
FIG. 16. Illustrates a close up of the cover member and the needle holder in the "unlocked" position.
Figure 17:
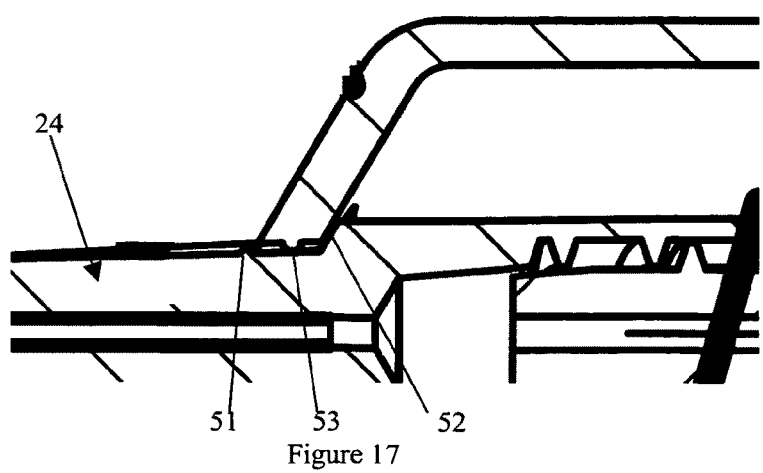
FIG. 17. Illustrates a close up of the cover member and the needle holder in the "locked" position.

The needle can be subsequently removed from the front of barrel 10 this being illustrated in FIGS. 5-6 and particularly in FIGS. 16-17. To do so, cover member 25 can simply be rotated in the other direction which will cause threading disengagement of the needle holder 24 with the projection 17. Of course, as this happens, the needle holder will move away from projection 17, this movement being allowed by the particular attachment of the cover member 25 to the needle holder 24. The particular arrangement is illustrated in FIGS. 16 and 17. Needle holder 24 has a recess part 50 and an annular rib or "bump" 51 in this part and spaced away from a rear inclined shoulder 52. In the arrangement of FIG. 16 the bump 51 is behind the cover member 25 and it is possible for the shoot back mechanism to operate to retract the needle holder leaving the cover member 25 behind and still attached to the front of the syringe.

However, the sliding arrangement can present a difficulty because once the needle holder 24 has been released from projection 17, and cover member 25 is pulled off the front of barrel 10, it will not remain attached to the needle holder 24. To prevent this, small locking tabs (the bump 51) is provided on the needle holder 24 that lock over member 25 as the needle holder is disengaged from the front of projection 17 (and therefore moves forwardly). This forward movement causes the bump 51 to engage with the cover member 25 such that the needle holder 24 can no longer be removed from the cover member 25. Once this happens, the cover member 25 can be pulled free from the front of barrel 10 and needle holder 24 will remain attached to the cover member 25. Of course, it may be desirable to replace cap 29 before doing so. Cover member 25 also has a circular rib or "bump" 53 which is within the recess part 50. Upon rotation of the cover member 25 in one direction, needle holder is threadingly released from to projection 17 and thus moves forwardly. Bump 51 will move towards bump 53 and at some stage will flex past bump 51 to the position illustrated in FIG. 17. Bump 53 (and therefore cover member 25) is trapped between bump 51 and inclined shoulder 52, and this causes the needle holder 24 to be attached to the cover member 25 so that when the cover member 25 is removed from the syringe it takes the needle holder 24 with it, and the needle holder 24 (containing the needle) does not just fall off which would be quite dangerous.

Once the needle has been removed, a new needle can be attached in the manner described with reference to FIGS. 1-3.

Referring again to FIG. 7-8, this illustrates the shoot back mechanism that has been described previously. However, it is now evident that as needle holder 24 is attached to body 11, retraction of body 11 will also shoot back the needle holder and puncture needle 23 into the interior of plunger 19. Importantly, cover member 25 stays on the front of barrel 10 and must not interfere with the retraction mechanism. For this reason, the small locking tabs 30 (see FIG. 7) are positioned behind the cover member 25 such that retraction into the plunger is not impeded as the locking tabs 30 are not locked to cover member 25. The only time that the locking tabs are attached to the cover member 25 is if the needle 23 is removed from the front of the syringe is as illustrated in FIGS. 5-6.

As mentioned previously, body 11 is held against retraction by a small frangible portion 15. The frangible portion can also be inadvertently and prematurely broken if body 11 is twisted. As attachment of needle holder 254 to the body is via a twisting action, there is a danger that body 1 can be subjected to a twisting force. To prevent this, anti-rotation means is provided. Typically, a part 31 (see FIGS. 1 and 1A) of the body 11 that passes through the front opening in barrel 10 contains longitudinal spines that engage with recesses or cutouts about the front opening. This prevents body 11 from rotating but does not prevent body 11 from retracting upon triggering of the shoot back mechanism. Of course, it is equally possible for part 31 to contain recesses and the opening in barrel 10 to contain projections again to prevent rotation while allowing retraction.

Referring now to the second embodiment of the invention which is described in FIGS. 9-14, this embodiment again allows the needle to be attached and removed to a syringe of the type having a shoot back mechanism, the primary variation being that the shoot back mechanism contains the female socket and the needle holder contains the projection, and a cover member is not provided.

Referring initially to FIG. 9, there is illustrated barrel 10 containing a shoot back mechanism in the form of body 11 biased by spring 13 and held in place by a ring 14 containing a frangible portion, this being substantially identical to that described with reference to the first embodiment of the invention. In the second embodiment, body 11 does not project from the front of barrel 10. Instead, the end of body 11 contains a socket 40 formed with an internal thread. The front of barrel 10 still contains an opening 41 as is common. Again, anti-rotation means are provided which may comprise projections on recesses similar to that described above, although this time the anti-rotation means may be provided within barrel 10.

The needle assembly comprises a needle 23 which is fitted to a needle holder 42. The needle holder 42 has a projecting outer end 43 which is threaded and which is adapted to engage with the socket 40 in body 11. A cap 44 is provided to protect needle 23.

In use, the needle assembly can be threadingly attached to body 11 in the manner best illustrated in FIG. 10. Once attached, the cap 44 can be pulled away to reveal the puncture needle 23. This is best illustrated in FIG. 11.

As a cover member of the type illustrated and described in the first embodiment is not present, should the needle be removed from the front of syringe 10, it is preferable to reattach cap 44 is illustrated in FIGS. 12-13. Referring particularly to FIG. 12, it can be seen that cap 44 contains a longitudinal slot 45 to enable needle 23 to pass through slot 45. Although the needle could also simply be pushed into the open end of cap 44, this can risk a needlestick injury. It is considered that passing the exposed needle through the elongate slot 45 is a safer way to house the needle within cap 44. Once attached (see FIG. 13), the needle assembly can be removed simply by counter rotation (see FIG. 14). The arrangement is such that if the needle 23 and needle holder 42 are attached to body 11, and if the retraction mechanism is triggered, the releasable arrangement of the needle holder to body 11 does not interfere with the retraction mechanism. Thus, in the second embodiment of the invention, the needle can still be retracted.

Throughout the specification and the claims (if present), unless the context requires otherwise, the term "comprise", or variations such as "comprises" or "comprising", will be understood to apply the inclusion of the stated integer or group of integers but not the exclusion of any other integer or group of integers.

Throughout the specification and claims (if present), unless the context requires otherwise, the term "substantially" or "about" will be understood to not be limited to the value for the range qualified by the terms.

It should be appreciated that various other changes and modifications can be made to any embodiment described without departing from the spirit and scope of the invention.

What is claimed is:

1. A needle-containing medical device comprising:
   a needle assembly which contains a needle and a needle holder to which the needle is attached,
   a housing having a front portion and a rear portion,
   a retractable body in the front portion of the housing and able to be retracted from a front position to a rear portion of the housing,
   a retraction mechanism comprising a biasing means to bias the retractable body to the rear portion of the housing, a holding means to hold the retractable body in the front of the housing against the bias, and a release means comprising a frangible portion that is broken by a plunger, the breaking of the frangible portion by the plunger triggering the biasing means to bias the retractable body to the rear portion of the housing;
   attachment means comprising a thread on the front of the retractable body and a thread on the needle holder that threadingly engages and disengages with the thread on the front of the retractable body to releasably attach to the needle holder thereby enabling the needle assembly to be removed from the retractable body and another needle assembly to be attached to the retractable body and to retract the needle assembly into the housing upon retraction of the retractable body; and
   anti-rotation means on the retractable body to prevent the retractable body from rotating relative to the retraction mechanism thereby preventing the frangible portion from breaking when the needle holder threadingly engages and disengages with the thread on the front of the retractable body.

2. The device of claim 1, comprising a cap to protect the needle, the cap able to be removed to expose the needle, the cap being attached to the needle holder.

3. The device of claim 2, wherein the biasing means is a spring.

4. The device of claim 1, comprising a cover member that extends about the needle holder such that the needle holder is at least partially within the cover member, the cover member adapted for releasable attachment to the housing.

5. The device of claim 4, wherein the cover member is adapted for rotation and is associated with the needle holder such that rotation of the cover member causes rotation of the needle holder and causes the needle holder to attach to or detach from the attachment means on the retractable body.

6. The device of claim 5, wherein the attachment means is a threading attachment means and the cover member is associated with the needle holder such that the needle holder can slide relative to the cover member.

7. The device of claim 6, comprising locking means to lock the needle holder to the cover member against further sliding movement such that removal of the cover member from the device also removes the needle holder which remains attached to the cover member.

8. The device of claim 7, comprising a removable cap protecting the needle, the cap being removably attached to the needle holder and in front of the cover member.

9. The device of claim 1, comprising a cap to protect the needle, the cap able to be removed to expose the needle, the cap being attached to the needle holder, the cap having a longitudinal slot through which the needle can pass to remove and to reattach the cap.

* * * * *